United States Patent [19]
Bennett et al.

[11] Patent Number: 5,429,105
[45] Date of Patent: Jul. 4, 1995

[54] CURRENT REPLICATION CIRCUIT AND METHOD FOR USE IN EXHAUST GAS OXYGEN MONITORING

[75] Inventors: Robert M. Bennett, Monument; David P. Laude, Colorado Springs, both of Colo.

[73] Assignee: Ford Motor Company, Dearborn, Mich.

[21] Appl. No.: 241,105

[22] Filed: May 11, 1994

Related U.S. Application Data

[63] Continuation-in-part of Ser. No. 24,017, Mar. 1, 1993, abandoned.

[51] Int. Cl.⁶ ............................................. F02M 7/00
[52] U.S. Cl. ................................................... 123/693
[58] Field of Search .............. 123/693, 672, 694, 695; 204/406, 425, 412, 431; 73/23

[56] References Cited

U.S. PATENT DOCUMENTS

| | | | |
|---|---|---|---|
| 4,153,023 | 5/1979 | Asano et al. | 123/693 |
| 4,214,563 | 7/1980 | Hosaka | 123/693 |
| 4,344,317 | 8/1982 | Hattori et al. | 73/23 |
| 4,355,615 | 10/1982 | Asano et al. | 123/693 |
| 4,615,787 | 10/1986 | Yamada et al. | 204/406 |
| 4,665,874 | 5/1987 | Kawanabe et al. | 123/440 |
| 4,698,209 | 10/1987 | Hashimoto et al. | 422/88 |
| 4,721,084 | 1/1988 | Kawanabe et al. | 123/440 |
| 4,762,604 | 8/1988 | Asakura et al. | 204/406 |
| 4,767,520 | 8/1988 | Asakura et al. | 204/406 |
| 4,792,387 | 12/1988 | Ishihara et al. | 204/425 |
| 4,796,587 | 1/1989 | Nakajima et al. | 123/440 |
| 4,877,511 | 10/1989 | Nakajima et al. | 204/406 |
| 4,915,813 | 4/1990 | Nakajima et al. | 204/406 |
| 4,981,125 | 1/1991 | Kato et al. | 123/440 |
| 5,211,154 | 5/1993 | Brandt | 123/693 |

FOREIGN PATENT DOCUMENTS

| | | |
|---|---|---|
| 121905 | 10/1984 | European Pat. Off. |
| 190974 | 8/1986 | France |

OTHER PUBLICATIONS

8090A IEEE Transactions on Circuits and Systems, I: Fundamental Theory and Applications 39 (1992) Oct., No. 10, New York, U.S.

*Primary Examiner*—Raymond A. Nelli
*Attorney, Agent, or Firm*—Richard D. Dixon; Roger L. May

[57] ABSTRACT

A method and circuit for generating an output signal representative of the pumping current required to equalize the oxygen diffusion between the sensing cell and the pumping cell of an oxygen-ion concentration proportional sensor located in the exhaust system of an internal combustion engine. A replication current, which is isolated from but representative of the pumping current, is generated. The replication current is then passed through a load resistance for generating the output signal. The replication current is generated simultaneously with but isolated from the pumping current, thereby eliminating the need for separate amplification of a sensed version of the pumping current.

15 Claims, 3 Drawing Sheets

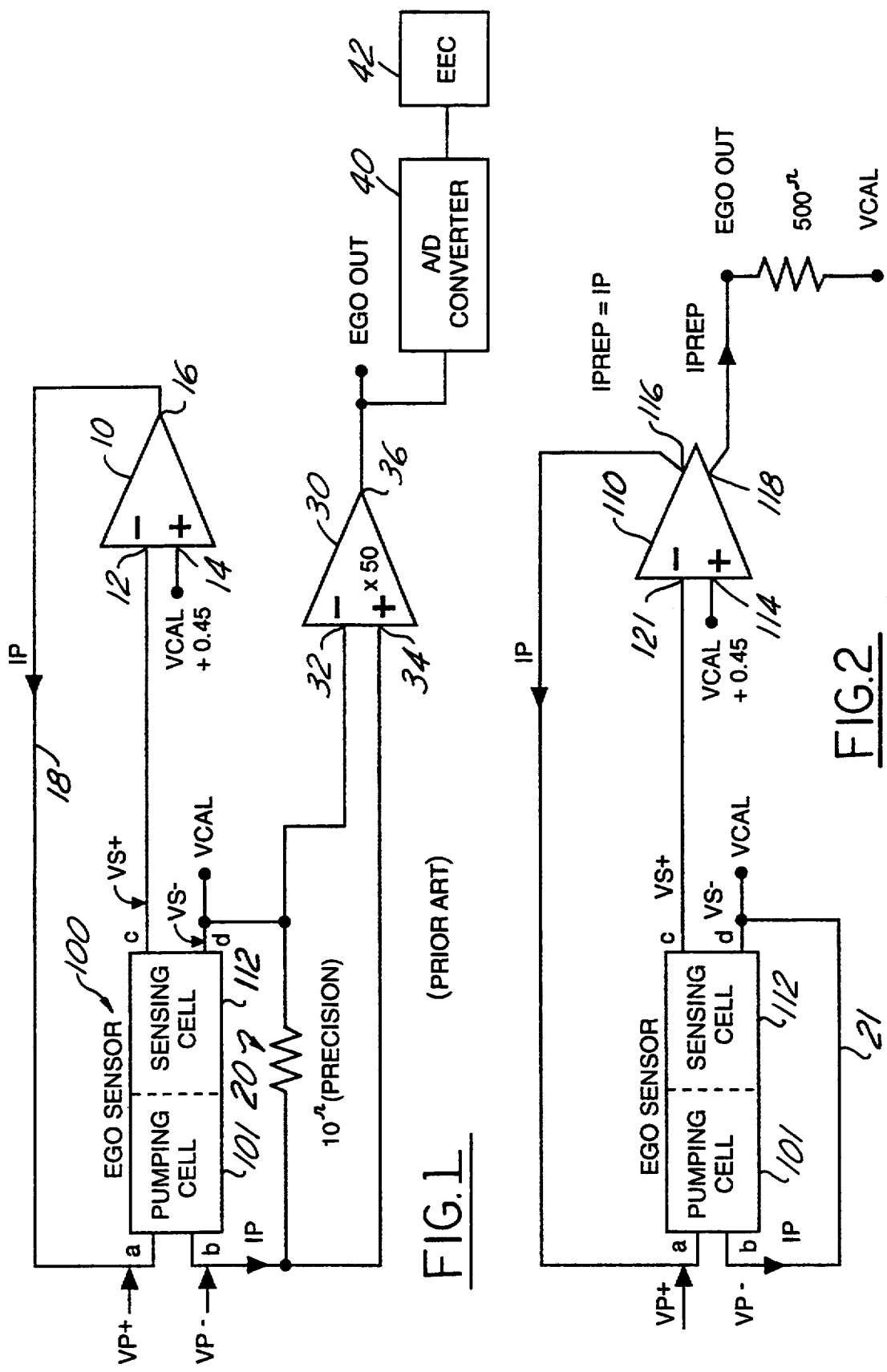

CURRENT REPLICATION CIRCUIT AND METHOD FOR USE IN EXHAUST GAS OXYGEN MONITORING

CORRESPONDING APPLICATIONS

This application is continuation in part application of application Ser. No. 08/024,017, filed Mar. 1, 1993 now abandoned.

BACKGROUND OF THE INVENTION

Field of the Invention

The present invention relates to circuits used with oxygen-ion concentration proportional sensors located in the exhaust system of an internal combustion engine and coupled to an air-fuel ratio control system for the internal combustion engine.

Description of the Prior Art

An oxygen-ion concentration proportional sensor that is well-known in the prior art. The sensor includes first and second elements that converge at a common wall to form a body of the sensor. The body defines therein a reference gas chamber that is open to a source of ambient air and an exhaust gas chamber that is coupled through a gas flow slit to the exhaust system of an internal combustion engine.

The body and wall elements are formed from a solid electrolytic material having oxygen-ion conductivity that may be formed from zirconium dioxide for example. Electrodes are formed on opposing sides of a common wall to constitute a pumping cell and on opposing sides of the body element to form a sensing cell. An electrical heater element is coupled to a surface of the body element for heating the entire structure to approximately 800° Celsius in order to activate the entire oxygen sensor.

Under these conditions if a constant voltage is maintained across the electrodes of the sensing cell, then the pumping current flowing through the cells will be proportional to the oxygen content of the adjacent gases. Under operating conditions, the oxygen content of the adjacent gasses will vary with the changes in the oxygen content of the exhaust gasses produced by the internal combustion engine, and the pumping cell current is adjusted by the control electronics to maintain a constant sensing cell voltage. In this manner the resulting pumping cell current is a direct indication of the oxygen content in the exhaust gasses being monitored.

FIG. 1 illustrates a circuit for being used with the prior art EGO sensor described above. A high gain differential amplifier 10 includes a negative input 12, a positive input 14 and an output 16. The negative input 12 is connected to terminal c of the sensing cell 100 in the Exhaust Gas Oxygen sensor (EGO sensor) 100. The positive input 14 of the high gain differential amplifier 10 is coupled to a calibration voltage VCAL plus a bias voltage of 0.45 volts, while the output 16 is coupled through an electrical conductor to an input a of the pumping cell 101 of the EGO sensor 100.

A series precision 10 ohm resister 20 has one end coupled to terminal b of the pumping cell 101 and the other end coupled to terminal d of the sensing cell 112 in the EGO sensor 100. The two inputs 32 and 34 of a differential amplifier 30 having a gain of 50 are coupled across the resistor 20, and an output 36 of the differential amplifier 30 represents the output voltage "EGO out" representative of the oxygen content sensed by the EGO sensor. This output voltage is then coupled through an analog to digital converter 40 and into the electronic engine control system 42 of the vehicle.

The output 16 from the high gain differential amplifier 10, which is coupled through conductor 18 back to terminal a of the pumping cell 101 of the EGO sensor 100, closes an electrical feedback loop from the sensing cell 112 to the pumping cell 101. This feedback loop maintains the sensing cell voltage, which is equal to 0.45 volts in this example, by adjusting the pumping current (IP) from the output 16 of the high gain differential amplifier 10 to provide the required oxygen diffusion into the sensing cell 112. In normal operation the high gain differential amplifier 16 forces whatever pumping current is required through the conductor 18 in order to maintain the same voltage at the two inputs 12 and 14 of the high gain differential amplifier 10, which in the case of the preferred embodiment is equal to VCAL +0.45 volts.

For example, if the oxygen content in the exhaust gases were to be too high, which corresponds to the internal combustion engine running too lean, then the voltage from the sensing cell 112 would decrease at the input 12 to the differential amplifier 10. Since the second input 14 to the differential amplifier 10 is held constant, the decreasing voltage level at the first input 12 would result in the voltage at the output 16 going higher, thereby increasing the pumping current in conductor 18 in the positive direction. This in turn would cause the pumping cell 101 to pump oxygen away from the sensing cell 112, which would then bring the voltage at output terminal c of the sensing cell 112 and at the input 12 of the differential amplifier 10 back down to VCAL plus 0.45 volts.

With continuing reference to the prior art embodiment illustrated in FIG. 1, the pumping current IP exits the pumping cell 101 at terminal b and flows through the precision 10 ohm series resistor 20 which terminates at terminal d of the sensing cell 112. A differential amplifier 30 multiplies the voltage developed across resistor 20 by a linear factor of 50. The EGO output voltage at output 36 is then monitored by the input of the analog to digital converter 40 and the engine control system 42.

If the oxygen content in the engine exhaust gas is lower than the calibrated level, then more oxygen is pulled into the sensing cell 112 from the pumping cell 101 in order to maintain the 0.45 volt bias characteristic of the EGO sensor 100. If the oxygen in the exhaust gas is higher than the calibrated level, then the pumping cell 101 removes oxygen from the sensing cell 112 in order to maintain the 0.45 volt bias. The pumping rate, either in the positive or the negative direction, depends on the magnitude of the pumping current. Also, the direction of the oxygen pumping is controlled by the direction of the pumping current flowing through conduct 18.

In the embodiment illustrating the prior art as shown in FIG. 1, for an EGO output voltage that varies from 0 to 5 volts at the output 36 of the differential amplifier 30, and assuming that the calibration voltage at terminal d of the sensing cell 112 is equal to 2.5 volts, then for a pumping current equal to zero the EGO output from the output 36 of the differential amplifier 30 will be equal to 2.5 volts. This example assumes that resistor 20 is 10 ohm resistor and that the gain of the differential amplifier 30 is set to approximately 50.

In order for the circuit to operate under conditions corresponding to the lowest possible internal combustion engine emissions, it is necessary for the EGO sensor to operate with the output voltage from terminal b of pumping cell 101 (hereinafter called VP−) to be very close in potential to the input at terminal d of the sensing cell 112 (hereinafter VS−). In order to minimize the voltage drop between VP− and VS−, which under ideal circumstances should be zero, the resistance of resistor 20 should be reduced to a very low value. The prior art teaches that the maximum voltage across resistor 20 should be less than 50 millivolts (0.005 amps × 10 ohms), but this requires that the resulting small signal voltage developed across resistor 20 be amplified by a factor of 50 in order to develop a sufficient full scale signal swing for optimum operation of the Analog to Digital Converter (ADC). Since the ADC can resolve voltages only as low as five to 10 millivolts, the signal at the output 36 of the differential amplifier 30 must be as large as possible in order for the system to detect small variations in the oxygen content of the exhaust gases. Amplification of the voltage developed across the sensing resistor 20 by a factor of 50 is prone to noise and errors, because any noise at the input terminals 32 and 34 of the differential amplifier 30, together with any offset voltages that may be present at the input terminals, will be amplified by a factor of 50 along with the signals. In a monolithic integrated circuit that integrates amplifiers 10 and 30, and the EGO heater control circuits, it would be impossible to completely isolate the noise generated by these circuits from the inputs 32 and 34 of the differential amplifier 30. The solution taught in the prior art is a compromise between how much noise and error can be tolerated by the differential amplifier 30, and how much error can be tolerated by allowing a voltage difference across the sensing resistor 20.

Another problem leading to performance degradation of the sensing system relates to that non-linear current and voltage characteristics (I-V curve) around the region where the pumping current is near zero. This region of operation is critical because it occurs when the engine is being controlled within the lowest emissions levels. In the voltage driven scheme for the pumping cell as used in the prior art, the output 16 of the amplifier 10 is a controlled voltage source. When the pumping cell goes through the non-linear region, a sudden change of voltage is required to change the pumping current just slightly. This requires the amplifier 10 to operate very quickly to cause the required change in voltage at its output 16. In reality, this change in output voltage takes a significant period of time due to finite slew rate of the internal amplifier nodes in the signal path being driven by the amplifier. During this delay, the pumping current is in error and the performance of the engine is degraded. If the pumping cell were driven by an amplifier with a current output and a replication of the pumping current could be generated in a circuit that is decoupled from the full loading effects of the pumping and sensing cells, then a more accurate tracking of the pumping current replication could be achieved in the critical low emissions region of the engine operating curve.

Therefore, it is a primary object of the present invention to reduce the noise and unwanted offset voltages of the EGO output signal by eliminating the need to amplify the noise and offset components by the amplification factor of the differential amplifier 30.

SUMMARY OF THE INVENTION

A method and circuit are provided for generating an output signal representative of the pumping current required to equalize the oxygen density between the sensing cell and the pumping cell in an oxygen-ion concentration proportional sensor located in the exhaust system of an internal combustion engine. The method includes the step of generating a replication current isolated from but representative of the pumping current, whereby the unwanted noise is not amplified and the offset components are eliminated. The replication current is then passed through a load resistance of sufficient value for generating the output signal of required magnitude.

The circuit includes a calibration signal generator for generating a reference voltage. A differential amplifier having inputs coupled to the output of the sensing cell and to the calibration voltage compares the output voltage from the sensing cell with the reference voltage and responsive thereto generates an output voltage representative of the pumping current. The first output of the differential amplifier is coupled to an input of the pumping cell for providing pumping current to energize the pumping cell. The output of the pumping cell is coupled to the input of the sensing cell and to the calibration means without the use of a series sensing resistor. A replication current generator is coupled to the differential amplifier for generating, at an output thereof which is isolated from the first output, a replication current isolated from the pumping current IP. A series load resistance is coupled between the output of the replication current generator and the calibration generator for generating thereacross the output signal responsive to the flow of the replication current therethrough, whereby the output voltage across the series load resistance will be representative of the pumping current.

BRIEF DESCRIPTION OF THE DRAWINGS

Other objects, features and advantages will be apparent from the study of the written description and the drawings in which:

FIG. 1 is a schematic block diagram showing the circuits used in conjunction with prior art EGO sensors.

FIG. 2 illustrates a schematic block diagram of a first preferred embodiment of the present invention which eliminates the use of a series sensing resistor between the pumping cell and the sensing cell.

DESCRIPTION OF THE PREFERRED EMBODIMENT

Figure 3:
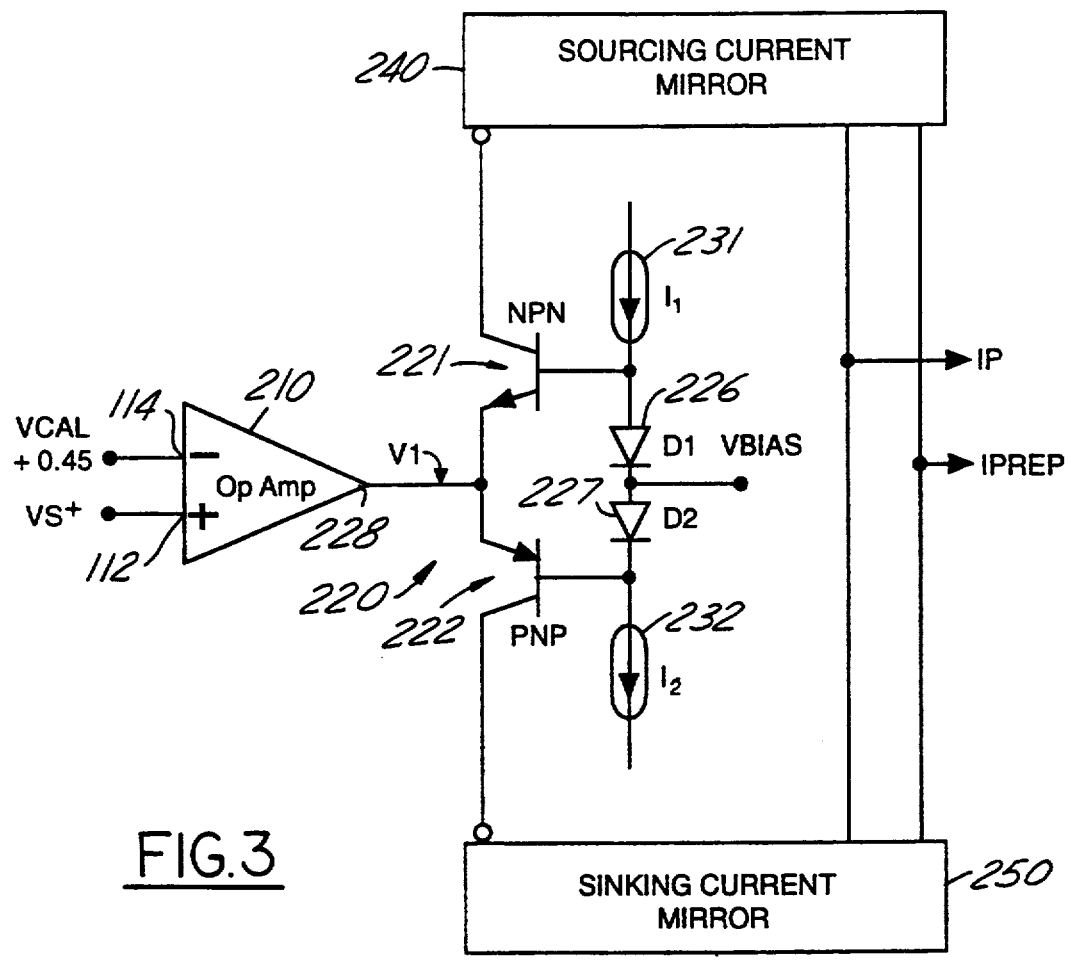
FIG. 3 illustrates a simplified schematic block diagram of the current mirror in accordance with the first preferred embodiment illustrated in FIG. 2.

A first preferred embodiment of the present invention is illustrated in FIG. 2, which is generally the same as the block diagram shown in FIG. 1 with the following exceptions. First, series sensing resistor 20 in FIG. 1 has been replaced with a conductor 21 so that no series sensing resistors are used. This eliminates a major source of error, in that VP− is now generally equal to VS−, and there is no voltage drop induced by the pumping current IP flowing through the series resistor 20. Secondly, the high gain differential amplifier 10 with the single output 16 has been replaced with the high gain differential amplifier 110 having a negative input 121 corresponding to the negative input 12 of amplifier 10 and having a positive input 114 corresponding to the positive input 14 on the prior art differential amplifier 10. The differential amplifier 110 also includes a first output 116 that corresponds to the first output 16 of the prior art differential amplifier 10, but the new amplifier 110 also includes a second output 118. The output pumping current IP from the first output 116 is equivalent to the pumping current IP from the differential amplifier 10 utilized in the prior art, but the output current from the second output 118 is designated as IPREP, which is a replication of the original pumping current from the first output 116. The replicated pumping current IPREP is a faithful replication of the pumping current developed in the feedback loop comprising the pumping cell 101, sensing cell 112 and the high gain differential amplifier 110.

Since the second differential amplifier 30 illustrated in the prior art of FIG. 1 is no longer required, the replication current IPREP can be directed through a series precision resistor 120 having a resistance of 500 ohms. The other end of the series resistor 120 is then connected to VCAL, which is approximately 2.5 volts. Since the new series resistor 120 is 50 times larger than the prior art series resistor 20 (500 ohms versus 10 ohms), the replicated pumping current IPREP directly produces the EGO output voltage across resistor 120 without the need for any additional amplification as utilized in the prior art. Therefore, the noise and the offset components produced by amplifier 30 are not amplified as in the prior art embodiment shown in FIG. 1.

When the replicated pumping current IPREP is zero, the EGO output at output 118 of differential amplifier 110 becomes 2.5 volts (equal to VCAL) as in the prior art because resistor 120 is terminated into VCAL. In this manner, digital to analog converter circuits and the EGO heater control circuits can be more readily integrated into a monolithic integrated circuit, since any noise generated by these circuits will not be amplified as with the prior art solutions. The ability to integrate all of the required EGO functions into a single monolithic integrated circuit greatly assists in minimizing the cost of this relatively expensive emission control circuit.

The preferred embodiment of the present invention requires precision in how well the pumping current IP and the replicated pumping current IPREP match each other. Some degree of current gain precision is required in the lean burn region of operation, wherein IP will be greater than zero. The most stringent requirement occurs near the ideal air/fuel ratio when the pumping current IP is near zero. This precision requirement calls for a very low offset current error, which is defined as the replication current IPREP that exists at the output 118 of differential amplifier 110 when the pumping current IP at the first output 116 is equal to zero.

A simplified schematic diagram of the differential amplifier 110 of FIG. 2 is shown in more detail in FIG. 3. The amplifier includes a conventional operational amplifier (op-amp) 210 having a negative input 114 and a positive input 112. An output of the operational amplifier 210 is coupled to a current steering circuit 220 comprising npn transistor 221 and pnp transistor 222. Transistor 221 and 222 are quiescently biased by diodes 226 and 227, by current generators 231 and 232, and with the bias voltage VBIAS so that when very small values of pumping current IP are required a minimal but necessary amount of operating bias current flows through the current replication circuitry 220. When pumping current IP is required to source current to a load, the positive input 112 of the operational amplifier 210 falls off slightly below the negative input 114. The operational amplifier 210 responds by pulling output 228 in a negative direction. The resulting decrease in the voltage at output 228 increases the current flow through the collector of transistor 221 which feeds the sourcing current mirror 240. A current mirror, comprising a sourcing current mirror 240 and a sinking current mirror 250, utilizes conventional precision current mirror techniques.

The collector current of transistor 221 is converted into two sourcing currents, the pumping current IP and the replicated pumping current IPREP. The pumping current IP, operating through the pumping cell 101, forces the positive input 114 of the op-amp 210 back up to VCAL plus a bias offset of 0.45 volts. When the pumping current is required to sink current, then the collector current of transistor 222 increases and the sinking current mirror 250 provides the pumping current IP and the replicated pumping current IPREP.

While conventional current mirrors have been illustrated in the preferred embodiment, the difference between the output voltage from the sensing cell and the reference voltage could be used to drive two (or more) separate current sources, one for generating the pumping current and another for generating the replication current, provided that the current sources are matched to produce isolated output currents in the required ratio. The matching of the two current generators over the expected operating range, and especially in the low current ranges, is important to the proper operation of the system.

Unlike some current mirror applications, in the present embodiment it is not necessarily important how well the output currents, IP or IPREP, scale to the input current, but rather how well the replicated pumping current IPREP tracks the original pumping current IP. The present embodiment allows for significant mismatches to occur between the current gains of the sourcing current mirror 240 and the sinking current mirror 250, because only one of the current mirrors can be conducting current at any given time, except for the small quiescent current that flows when pumping current is essentially equal to zero. However, it is important that the quiescent currents of both IP and IPREP are well matched.

An optional feature, referred to as selective voltage gain or selective voltage gain, may be utilized with the first preferred embodiment of the present invention. For operational regions near the ideal air/fuel ratio, the pumping current IP is very small. If the replicated pumping current IPREP could become an amplified version of the pumping current IP in this area of interest, then greater accuracy could be achieved in the measurement of the ideal air/fuel ratios for enhanced engine emission control.

Figure 4:
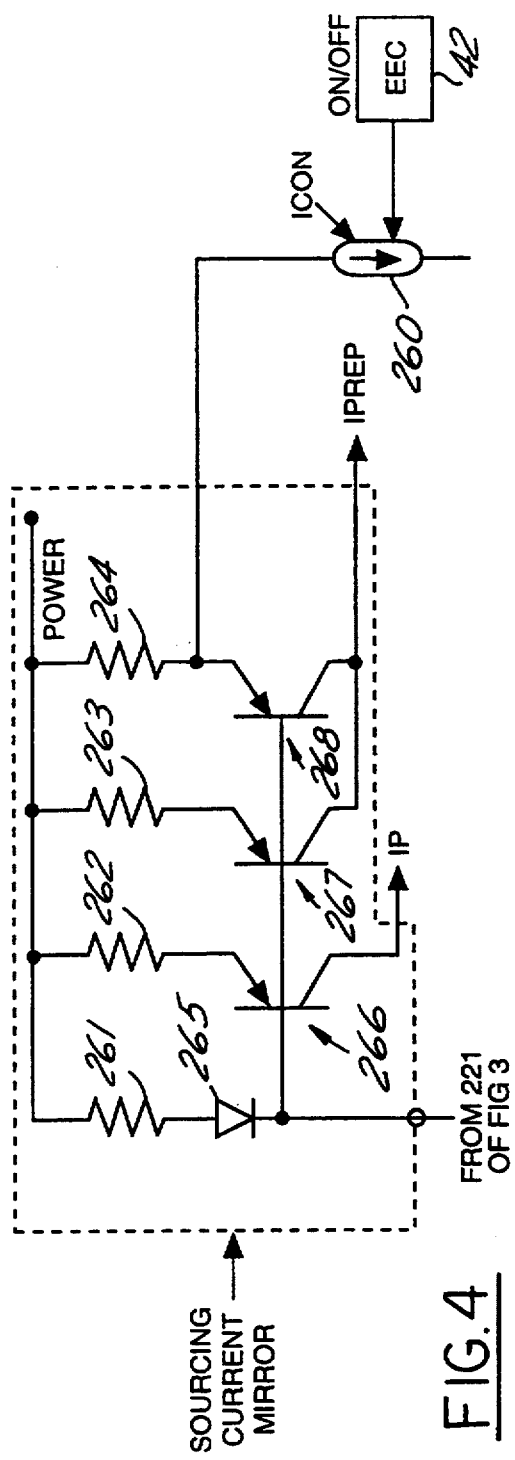
FIG. 4 is a simplified schematic diagram of a current mirror in accordance with the circuitry illustrated in FIG. 3.

FIG. 4 illustrates an idealized schematic diagram of a digitally controlled embodiment having several different current gains between IP and IPREP. When IP and IPREP are desired to be equal, then the current sink ICON 260 is turned on by a control signal coupled to the electronic engine control system. When current sink ICON 260 is on, then a sufficient voltage is developed across resistor 264 such that transistor 268 is turned off for any reasonably anticipated bias across resistor 261 and diode 265. Under these conditions, sufficient device matching error can occur such that IP and IPREP may match only within a few percent at best. A commutation method for canceling the effects of this mismatching error will be discussed subsequently.

Because the values of resistor 262, 263 and 264 are ideally equal, and since transistors 266, 267 and 268 are ideally identical, the collector currents of transistors 266 (IP) and 267 (IPREP) are identical. Therefore, the pumping current IP will be equal to the replicated pumping current IPREP. In the case where the replicated pumping current IPREP is desired to be twice as large as the pumping current IP, then the current sink ICON 260 is turned off by the digital control. Now, IPREP is equal to the sum of both the collector currents from transistors 267 and 268, which are equal to twice that of the collector current from transistor 266. It should be apparent to one skilled in the art that field effect transistors, bipolar transistors or a combination of both could be used to realize these desired functions.

The operating accuracy of a monolithic integrated circuit implementation of the preferred embodiment can be enhanced further by eliminating the effects of temperature drift and mismatch of the components. This accuracy can be increased greatly by commutating the two current levels, IP and IPREP, with a fixed duty cycle, for example a 50% duty cycle in the preferred embodiment. This switching or substitution of IP and IPREP has the effect of averaging the two currents at a single output. This average value of the current at the output follows the form, where t1 is the on time for IP1 and t2 is the on time for IP2:

$$IP = (IP1*t1 + IP2*t2)/(t1+t2)$$

$$IPREP = (IP2*t1 + IP1*t2)/(t1+t2)$$

If t1 is equal to t2 for a 50% duty cycle, which may be accomplished with a slow speed clock signal, then the two currents reduce to $IP = IPREP = (IP1 + IP2)/2$. This commutation causes a significant improvement in accuracy since temperature, drift and offset biases are canceled. The only errors that remain relate to the clock switching transients and the current mismatch error in the switches themselves, which would be negligible if MOS or bipolar Darlington switches are used. While a 50% duty cycle is recommended where IP1 equals IP2, other duty cycles could be used as required in the specific applications where IP1 does not equal IP2.

Figure 5:
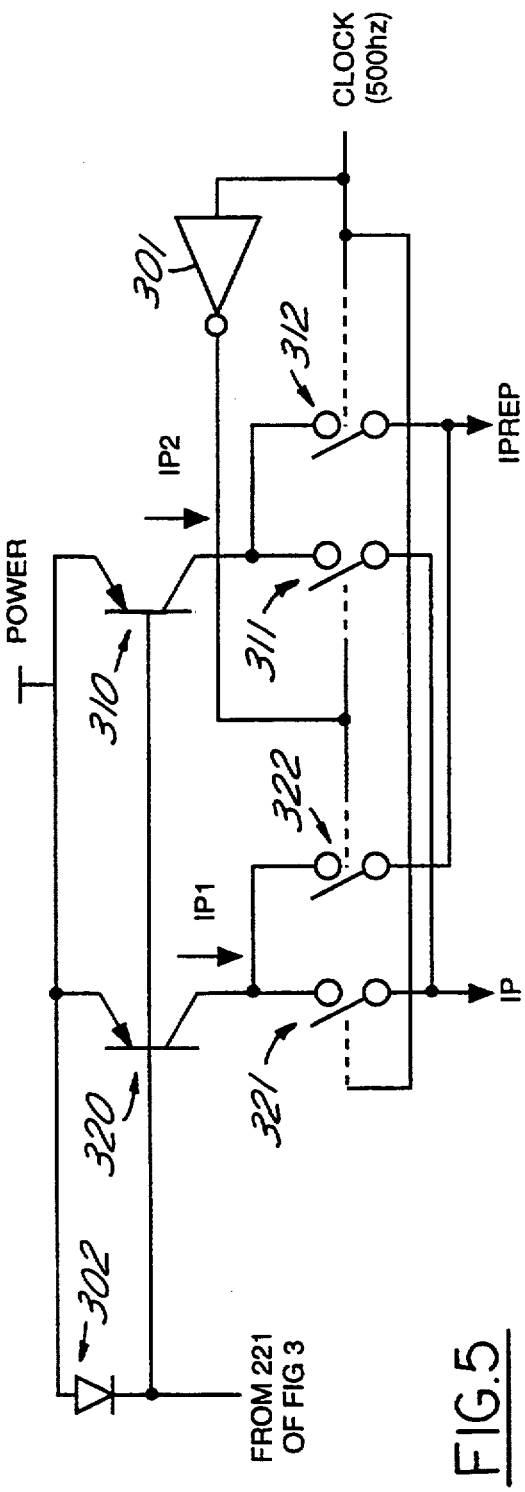
FIG. 5 illustrates a simplified schematic block diagram of a commutator circuit in accordance with the present invention.

FIG. 5 illustrates a simplified schematic diagram of a commutator circuit in accordance with the foregoing discussion. The output of transistor 221 in FIG. 3 is coupled through parallel connected transistors 310 and 320 and diode 302 to two pairs of commutating switches, 311/312 and 321/322, which are controlled by the inverting amplifier 301. These switches are commutated at a clock rate of approximately 500 Hz, which causes the output from transistor 310 (shown as IP2) to be switched first through switch 311 to the IP output and then through switch 312 to the IPREP output. In a similar manner, the output current from transistor 320 (shown as IP1) is commutated by switches 321 and 322 between IP and IPREP. While a clock rate of 500 Hz is utilized in the preferred embodiment, the clock frequency could be set from approximately 30 Hz to 10 KHz if required by specific applications.

Figure 6:
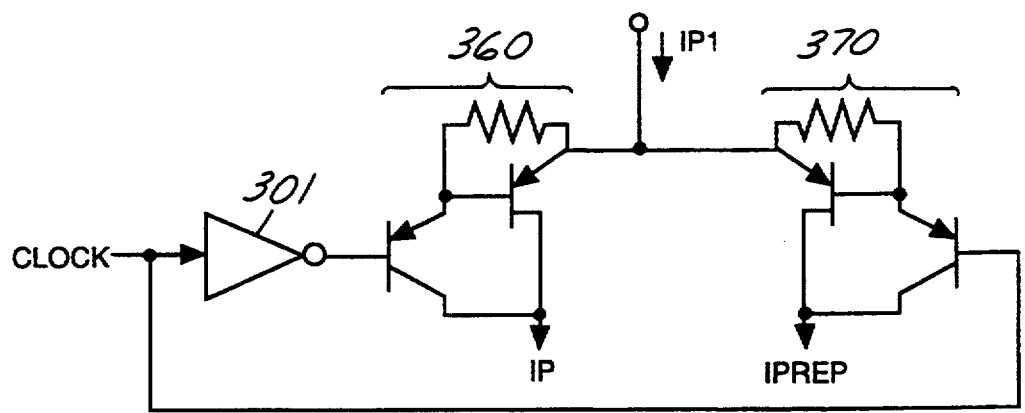
FIG. 6 illustrates a simplified schematic diagram of a commutator circuit in accordance with the block diagram shown in FIG. 5.

A bipolar transistor embodiment of the schematic illustrated in FIG. 5 is shown in more detail in FIG. 6. The pnp bipolar transistors are arranged as two Darlington pairs, 360 and 370, in order to reduce currents escaping from the commutator to the clock as base currents. If these escaping currents do not match sufficiently, then the commutator will present its own errors. By using Darlington pairs 360 and 370, the escaping currents are made small enough so that even if there is a mismatch the absolute current will be small. In FIG. 6, the clock voltage, which is assumed to be 50% duty cycle, will drive the inverting amplifier 301 to cause the Darlington pair 360 to conduct IP1 through to IP in part of the duty cycle, while in the other part of the duty cycle current IP1 is conducted by Darlington pair 370 to the output IPREP. It will be apparent that FIG. 6 illustrates a sourcing current commutator, and that sinking current commutators can be constructed by using n-type transistors, (e.g., n-channel MOSFETS or npn transistors).

As used herein, the term "commutation" is intended to represent the substitution of one signal, either voltage or current, for another according to a duty cycle that defines the relative ratio of the two signals. Various other communication circuits or devices could be used for this purpose with equally successful results. Furthermore, various active semiconductor devices may be substituted for those shown in the illustrations for generating the pumping and replication currents, provide that the other requirements specified herein are satisfied. It will be apparent that many modifications and variations may be implemented without departing from the scope of the novel concept of this invention. Therefore, it is intended by the appended claims to cover all such modifications and variations which fall within the spirit and scope of the invention.

We claim:

1. A method for generating an output signal representative of a pumping current required to equalize the oxygen diffusion between a sensing cell and a pumping cell of an oxygen-ion concentration proportional sensor located in an exhaust system of an internal combustion engine, comprising the steps of:
   (a) sensing the difference between an output voltage from said sensing cell and a reference voltage and responsive thereto simultaneously generating within a current mirror both said pumping current and a replication current, with said replication current being isolated from but representative of said pumping current, and
   (b) passing said replication current through a load resistance of known value for generating said output signal thereacross.

2. The method as described in claim 1 wherein step (a) includes the step of generating said replication current without the use of a series resistor for sensing said pumping current.

3. The method as described in claim 1 wherein step (a) also includes the step (a1) of generating said replication current as representative both in magnitude and polarity of said pumping current.

4. The method as described in claim 3 wherein step (a1) also includes the step of simultaneously generating at isolated outputs of said current mirror said pumping current and said replication current identical thereto.

5. The method as described in claim 1 wherein step (a) also includes the step of generating an amplified replication current representative of but amplified with respect to said pumping current when the magnitude of said pumping current falls below a predetermined minimum level, thereby providing an increased gain control for said output signal when said pumping current falls below said predetermined minimum level representative of low emission operation.

6. The method as described in claim 1 wherein step (a) further includes the steps of:
   (aa) generating said replication current isolated from but equal in magnitude and polarity with said pumping current, and
   (ab) commutating said replication current with said pumping current for passage through said load resistance, whereby any errors in generating said replication current will be reduced by periodically substituting said pumping current for said replication current.

7. The method as described in claim 6 wherein step (ab) further includes the step of regulating said commutating step to a 50% duty cycle.

8. A circuit for generating an output signal representative of the pumping current required to balance the oxygen diffusion between a sensing cell and a pumping cell in an oxygen-ion concentration proportional sensor located in the exhaust system of an internal combustion engine, comprising:
   calibration means for generating a reference voltage,
   differential amplifier means having inputs coupled to outputs of said sensing cell and said calibration means, for sensing an error voltage by comparing an output voltage from said sensing cell with said reference voltage and responsive thereto generating at an output thereof said pumping current,
   electrical connecting means coupled to said sensing cell, said pumping cell and said differential amplifier means for circulating said pumping current therethrough without the use of a series sensing resistance for sensing said pumping current,
   current replication means coupled to said differential amplifier means, for generating at an output thereof, isolated from said first output, a replication current isolated from but representative of said pumping current, and
   a series resistance coupled to said output of said current replication means for generating thereacross said output signal responsive to the flow of said replication current therethrough, whereby the output voltage across said series resistance will be representative of the pumping current.

9. The circuit as described in claim 8 wherein said current replication means comprises current mirror means for generating said replication current responsive to said pumping current.

10. The circuit as described in claim 8 wherein said replication current is equal in magnitude and polarity to said pumping current.

11. The circuit as described in claim 8 wherein said current replication means includes means for increasing the gain of said current replication means under conditions where said pumping current falls below a predetermined limit, thereby providing additional accuracy in the measurement of said pumping current under low emissions operation.

12. The circuit as described in claim 8 wherein said current replication means includes commutation means for periodically interchanging said replication current with said pumping current, and said pumping current with said replication current, whereby the effects of any errors in generating said replication current will be canceled.

13. A method for generating an output signal for controlling the air-to-fuel ratio in an internal combustion engine having an exhaust gas sensor of the type having a sensing cell and a pumping cell, comprising the steps of:
   a. sensing the difference between an output voltage from said sensing cell and a reference voltage, and responsive to said difference generating within a current mirror a first current representative of said pumping current for circulating through and controlling the operation of said sensing cell and said pumping cell, and
   b. simultaneously generating within said current mirror, responsive to said difference, a second current representative of a replication current isolated from but representative of said pumping current, and
   c. passing said replication current through a load impedance for generating said output signal.

14. The method as described in claim 13 wherein step (a) further includes the step of increasing the magnitude of said second current only when the magnitude of said first current falls below a predetermined minimum level indicative of low emission operation of said internal combustion engine, whereby said output voltage increases during low emission operation for providing increased output signal resolution and noise immunity.

15. The method as described in claim 13 wherein step (c) includes the preliminary step of commutating with a 50% duty cycle said first current with said second current for redefining said replication current before passage though said load impedance, whereby any errors in generating said replication current will be reduced by periodically substituting said first current for said second current.

* * * * *